United States Patent
Yamada et al.

(10) Patent No.: US 9,943,424 B2
(45) Date of Patent: Apr. 17, 2018

(54) ARTIFICIAL BLOOD VESSEL

(71) Applicant: Toray Industries, Inc., Tokyo (JP)

(72) Inventors: Satoshi Yamada, Otsu (JP); Hiroshi Tsuchikura, Otsu (JP); Nobuaki Tanaka, Otsu (JP); Kazuhiro Tanahashi, Otsu (JP); Yuka Sakaguchi, Otsu (JP); Masaki Fujita, Otsu (JP); Koji Kadowaki, Otsu (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/786,077

(22) PCT Filed: Apr. 23, 2014

(86) PCT No.: PCT/JP2014/061362
§ 371 (c)(1),
(2) Date: Oct. 21, 2015

(87) PCT Pub. No.: WO2014/175301
PCT Pub. Date: Oct. 30, 2014

(65) Prior Publication Data
US 2016/0058588 A1 Mar. 3, 2016

(30) Foreign Application Priority Data
Apr. 26, 2013 (JP) .................... 2013-093475

(51) Int. Cl.
*A61F 2/04* (2013.01)
*A61F 2/06* (2013.01)
(Continued)

(52) U.S. Cl.
CPC .............. *A61F 2/89* (2013.01); *A61F 2/06* (2013.01); *A61L 27/18* (2013.01); *A61L 33/068* (2013.01);
(Continued)

(58) Field of Classification Search
CPC . D10B 2509/06; A61F 2/06; A61F 2250/0017
See application file for complete search history.

(56) References Cited

U.S. PATENT DOCUMENTS

| 4,743,250 A | 5/1988 | Kitagawa et al. |
| 5,632,776 A * | 5/1997 | Kurumatani ............ A61L 27/18 424/423 |
| 2012/0226344 A1 * | 9/2012 | Shirokaze ............ D02G 1/0206 623/1.13 |

FOREIGN PATENT DOCUMENTS

| EP | 0 128 741 | 12/1984 |
| JP | 61-92666 A | 5/1986 |

(Continued)

OTHER PUBLICATIONS

Supplementary European Search Report dated Oct. 27, 2016, of corresponding European Application No. 14788777.2.

*Primary Examiner* — Dinah Baria
(74) *Attorney, Agent, or Firm* — DLA Piper LLP (US)

(57) ABSTRACT

An artificial blood vessel includes a tubular woven fabric composed of a multifilament yarn A including a first polyester and a multifilament yarn B including a second polyester, and has an inner diameter of 8 mm or less and a layer thickness of 50 μm or more and 250 μm or less, wherein the multifilament yarn A has a single fiber fineness of 1.0 dtex or more and a total fineness of 33 dtex or less, the multifilament yarn B has a single fiber fineness of 0.08 dtex or less and a total fineness of 66 dtex or less, and the multifilament yarn B forms loops on an inner wall surface of the tubular woven fabric.

4 Claims, 4 Drawing Sheets

(51) Int. Cl.
*A61F 2/89* (2013.01)
*A61L 27/18* (2006.01)
*A61L 33/06* (2006.01)
*D04B 21/02* (2006.01)

(52) U.S. Cl.
CPC ...... *D04B 21/02* (2013.01); *A61F 2210/0076* (2013.01); *A61F 2250/0017* (2013.01); *A61F 2250/0067* (2013.01); *D10B 2509/06* (2013.01)

(56) References Cited

FOREIGN PATENT DOCUMENTS

| | | | |
|---|---|---|---|
| JP | 64-62153 | A | 3/1989 |
| JP | 5-23362 | A | 2/1993 |
| JP | 2004-115976 | A | 4/2004 |
| JP | 2005-124959 | A | 5/2005 |
| JP | 2006-26155 | A | 2/2006 |
| WO | 97/43983 | | 11/1997 |

* cited by examiner

FIG. 1

ARTIFICIAL BLOOD VESSEL

TECHNICAL FIELD

This disclosure relates to an artificial blood vessel able to retain its mechanical properties and rarely undergoes the occurrence of thrombi-related clogging when grafted into a blood vessel having a small diameter.

BACKGROUND

Artificial blood vessels have been mainly used for the replacement of diseased blood vessels in living bodies or formation of bypasses. Therefore, artificial blood vessels are required to have good biocompatibility with hosts, non-toxicity or the like, be rarely deteriorated in living bodies and, therefore, tough, undergo a small volume of blood leakage, be antithrombogenic, not too expensive and the like.

Artificial blood vessels include artificial blood vessels made from cloths, artificial blood vessels made from polytetrafluoroethylene, artificial blood vessels derived from biomaterials, artificial blood vessels made from synthetic polymer materials and hybrid artificial blood vessels, and these artificial blood vessels are selected properly depending on intended use. For example, an artificial blood vessel made from a cloth has been mainly used as an artificial blood vessel for use in aortae having a large diameter (an inner diameter: 10 mm or more), and an artificial blood vessel made from a cloth and PTFE has been used frequently as an artificial blood vessel for use in arterial reconstruction in lower legs or the like which has a medium diameter (inner diameter: 6, 8 mm).

With respect to artificial blood vessels made from cloths, it has been demonstrated from long-term clinical tests that an artificial blood vessel made from polyester fibers is safe and practically useful as long as the artificial blood vessel has a medium or large diameter. However, when such an artificial blood vessel is used as an artificial blood vessel having a small diameter (an inner diameter: less than 6 mm), thrombi are formed in the artificial blood vessel and the artificial blood vessel cannot be kept in a patent state for a long period and, therefore, the practical usefulness of the artificial blood vessel for use as an artificial blood vessel for grafting applications is insufficient.

For the purpose of preventing the clogging and ensuring a sufficient patent state in the artificial blood vessel having a small diameter, a method of forming naps and/or loop-formed surface structures on the inner wall surface of the artificial blood vessel has been proposed (Japanese Patent Laid-open Publication No. 2005-124959), because the method can impart antithrombogenicity to the artificial blood vessel, in other words, enables rapid formation of endothelial cells on the inner wall surface of the artificial blood vessel.

However, when attempting to apply the technique disclosed in Japanese Patent Laid-open Publication No. 2005-124959 to an artificial blood vessel having a medium or small diameter, we found that the technique is not sufficient with respect to functions, properties and the like required for colonization of endothelial cells during grafting of the artificial blood vessel to a blood vessel having a medium or small diameter.

In those situations concerning the conventional artificial blood vessels, it could be helpful to provide an artificial blood vessel which can retain mechanical properties required for an artificial blood vessel and which rarely undergoes formation of thrombi and exhibits excellent cell adhesiveness when grafted into a blood vessel having a medium or small diameter.

SUMMARY

We thus provide:

(1) An artificial blood vessel comprising a tubular woven fabric which is composed of at least two types of polyester fibers, i.e., a multifilament yarn A and a multifilament yarn B, and has an inner diameter of 8 mm or less and a layer thickness of 50 µm or more and 250 µm or less, wherein the multifilament yarn A has a single fiber fineness of 1.0 dtex or more and a total fineness of 33 dtex or less, the multifilament yarn B has a single fiber fineness of 0.08 dtex or less and a total fineness of 66 dtex or less, and the multifilament yarn B forms loops on the inner wall surface of the tubular woven fabric.

In this description, the following are disclosed as preferred examples.

(2) The artificial blood vessel according to the above-mentioned item, wherein the number of single fibers in the multifilament yarn B that constitutes the tubular woven fabric is 40% to 80% of the number of single fibers that constitute the tubular woven fabric.

(3) The artificial blood vessel according to any one of the above-mentioned items, having a water permeability of 500 ml/min·cm$^2$·120 mmHg (16 kPa) or less.

(4) The artificial blood vessel according to any one of the above-mentioned items, wherein loops formed by the multifilament yarn B exist in a dispersed state or an irregularly interlacing state.

(5) The artificial blood vessel according to any one of the above-mentioned items, having the form of a bellows-type structure.

(6) The artificial blood vessel according to any one of the above-mentioned items, further comprising an antithrombogenic material.

The artificial blood vessel has the above-mentioned constitution and, therefore, it becomes possible to provide an artificial blood vessel which can exhibit effects as mentioned below, does not undergo formation of thrombi and, therefore, cannot be clogged, has long-lasting patency, is suitable for practical use, and has a medium or small diameter.

At least two types of polyester fibers, i.e., a multifilament yarn A having a single fiber fineness of 1.0 dtex or more and a total fineness of 33 dtex or less and a multifilament yarn B having a single fiber fineness of 0.08 dtex or less and a total fineness of 66 dtex or less, are used in combination, whereby it becomes possible to reduce deterioration in strength which may be caused by in vivo hydrolysis. Furthermore, when the above-mentioned at least two types of polyester fibers are used in combination, gaps between fibers tend to be formed more densely. Therefore, water permeability of the artificial blood vessel can have a proper value and leakage of blood rarely occurs. Still further, the above-mentioned combination enables improvement in cell colonization property and reduction in formation of thrombi. When fluffs or loops are formed in the artificial blood vessel, the artificial blood vessel can have improved neointima formability and, therefore, can be used suitably as an artificial blood vessel having a medium or small diameter.

When the number of single fibers that constitute the multifilament yarn B in the artificial blood vessel is adjusted to 40% to 80% of the number of single fibers that constitute the tubular woven fabric, the artificial blood vessel can have a more satisfactory cell colonization property, a more satisfactory strength retention property and a more satisfactory water permeability and, therefore, can be used suitably as an artificial blood vessel having a medium or small diameter.

When water permeability of the artificial blood vessel is limited to a value falling within a preferred range, leakage of blood from the artificial blood vessel can be prevented more effectively and, therefore, the artificial blood vessel can be used suitably as an artificial blood vessel having a medium or small diameter.

When the loops in the artificial blood vessel exist in a dispersed state or an irregularly interlacing state, fraying from an anastomosing part rarely occurs and, therefore, the artificial blood vessel can be used suitably as an artificial blood vessel having a medium or small diameter.

When the artificial blood vessel has a bellows-type structure, the artificial blood vessel can be imparted with excellent shape stability. Therefore, clogging, folding or kinking of the artificial blood vessel can be prevented and, therefore, the artificial blood vessel can be used suitably as an artificial blood vessel having a medium or small diameter.

When the artificial blood vessel further comprises an antithrombogenic material, formation of thrombi can be prevented and, therefore, the artificial blood vessel can be used suitably as an artificial blood vessel having a medium or small diameter.

DETAILED DESCRIPTION

The artificial blood vessel comprises a tubular woven fabric prepared using at least two types of polyester fiber multifilament yarns. The artificial blood vessel is composed of at least: a multifilament yarn A having a single fiber fineness of 1.0 dtex or more and a total fineness of 33 dtex or less; and a multifilament yarn B having a single fiber fineness of 0.08 dtex or less and a total fineness of 66 dtex or less.

As the multifilament yarn A, a yarn having a single fiber fineness of 1.0 dtex or more and a total fineness of 33 dtex or less can be used. The framework of the artificial blood vessel is formed by the fibers that satisfy the above-mentioned requirements, and the surface area in the artificial blood vessel on which hydrolysis may occur in vivo when the artificial blood vessel is placed in the body for a long period, can be reduced. Thus, the problem of deterioration in strength of the artificial blood vessel can be solved.

That is, if a multifilament yarn comprising filaments having a too small single fiber fineness is used, a surface area per mass of the fibers increases, the multifilament yarn is susceptible to hydrolysis and therefore greatly deteriorated in strength, and the artificial blood vessel framework-forming function of the multifilament yarn tends to become insufficient. If the total fineness is too large, gaps between fibers become too wide, water permeability becomes too high and, consequently, leakage of blood occurs frequently when the multifilament yarn is used in the artificial blood vessel. From the viewpoint of retention of strength and flexibility, the multifilament A has a single fiber fineness of 1.0 dtex or more, preferably 1.0 to 2.2 dtex, and also has a total fineness of 33 dtex or less, preferably 17 to 33 dtex.

As the multifilament yarn B, a multifilament yarn composed of filaments having a single fiber fineness of 0.08 dtex or less and having a total fineness of 66 dtex or less is used. The multifilament yarn B forms loops on at least the inner wall surface of the tubular woven fabric, whereby it becomes possible to impart a surface shape having an excellent cell colonization property to the inner wall surface of the tubular woven fabric. If a multifilament yarn composed of filaments having a single fiber fineness of more than 0.08 dtex is used, the gaps between single fibers become wider and the cell colonization property deteriorates. If a multifilament yarn having a too large total fineness is used, the thickness of a portion of the inner wall surface occupied by the loops is increased. As a result, a substance that can cause formation of thrombi such as fibrin can be captured easily and thrombi can be formed easily. From the viewpoint of a cell colonization property and an interlacing property, the single fiber fineness is 0.08 dtex or less, preferably 0.05 to 0.08 dtex. From the viewpoint of antithrombogenicity, the total fineness is 66 dtex or less, preferably 44 to 66 dtex.

The tubular woven fabric may be produced using a multifilament A and a multifilament yarn B each having the single fiber fineness and the total fineness specified herein. Alternatively, the tubular woven fabric may also be produced using the multifilament A and a multifilament that has a high single fiber fineness and a high total fineness and can be processed into an ultrafine fiber, and then the latter multifilament is processed into an ultrafine fiber by a chemical or physical means to produce a multifilament B having the single yarn fineness and the total fineness specified herein. The method of producing the ultrafine fibers is not particularly limited. Currently, many ultrafine fibers have been produced by a method employed to produce an ultrafine fiber having a so-called sea-island structure or a split-type structure. In production from a sea-island structure, a method in which the ultrafine fibers serve as island portions and a sea portion is dissolved is employed. Alternatively, a method in which the fibers are split in the length direction to produce the ultrafine fibers may also be employed. In this case, a polyamide-type polymer, a polyolefin-type polymer, polystyrene, a soluble polyester-type polymer or the like can be used as the sea portion or the split portion (with respect to the details of these methods of producing ultrafine fibers, see, for example, Okamoto M: Ultra-fine fiber and its application, Preprints Japan-China Bilated Symposium on Polymer Science and Technology, 256-262, Tokyo, October, 1981. When such fibers are used, even though the fibers keep their original diameters during formation of the tubular woven fabric, the fibers can be processed into an ultrafine fiber after formation of the tubular woven fabric and, therefore, occurrence of troubles during processing, including breakage of the yarn and formation of fluffs can be minimized during weaving or upon application of any one of various yarn processing means before weaving.

In the artificial blood vessel, polyester fibers are used as the fibers constituting the multifilament yarn A and the multifilament B. Examples of the polyester fibers include fibers made from polyethylene terephthalate, fibers made from polybutylene terephthalate and the like. Fibers made from a co-polyester produced by copolymerizing polyethylene terephthalate or polybutylene terephthalate with an acid component such as isophthalic acid, sodium 5-sulfoisophthalate or an aliphatic dicarboxylic acid, e.g. adipic acid, may also be used. In the above-mentioned fibers, the fibers constituting the multifilament yarns A and the fibers constituting the multifilament yarn B to be combined may be the same as each other or may be different from each other, and the fibers can be combined properly.

Figure 1:
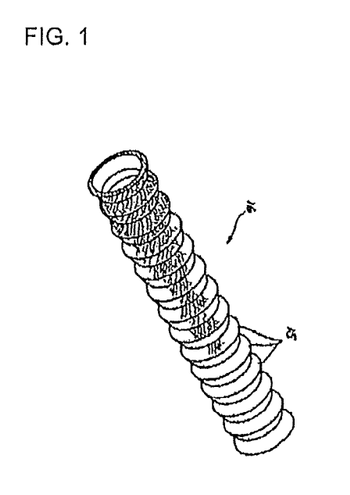
FIG. 1 is a schematic perspective view of an example of an artificial blood vessel having a bellows-type structure.
Figure 2A:
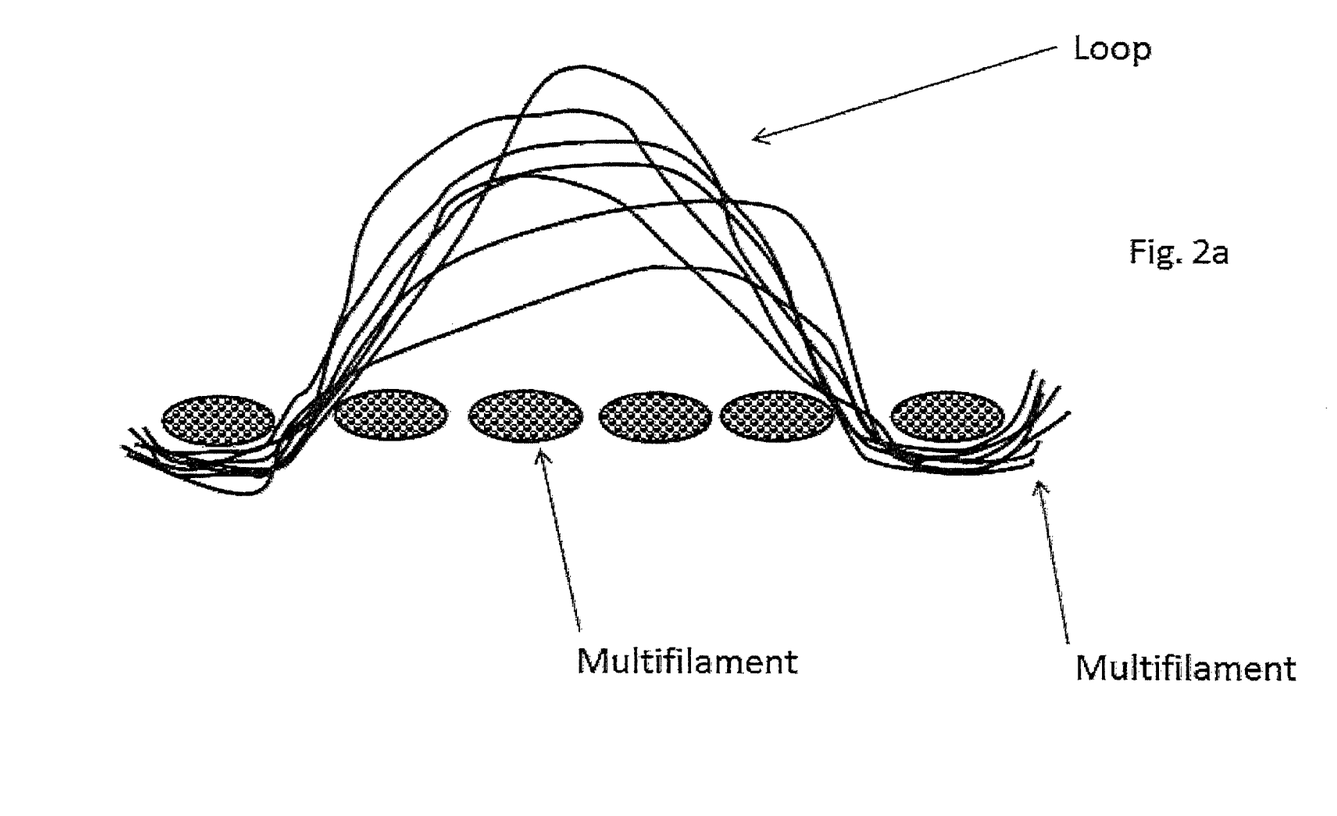
FIG. 2a shows a schematic cross-sectional view of loops formed from a woven satin of which a warp passes over four wefts.
Figure 2B:
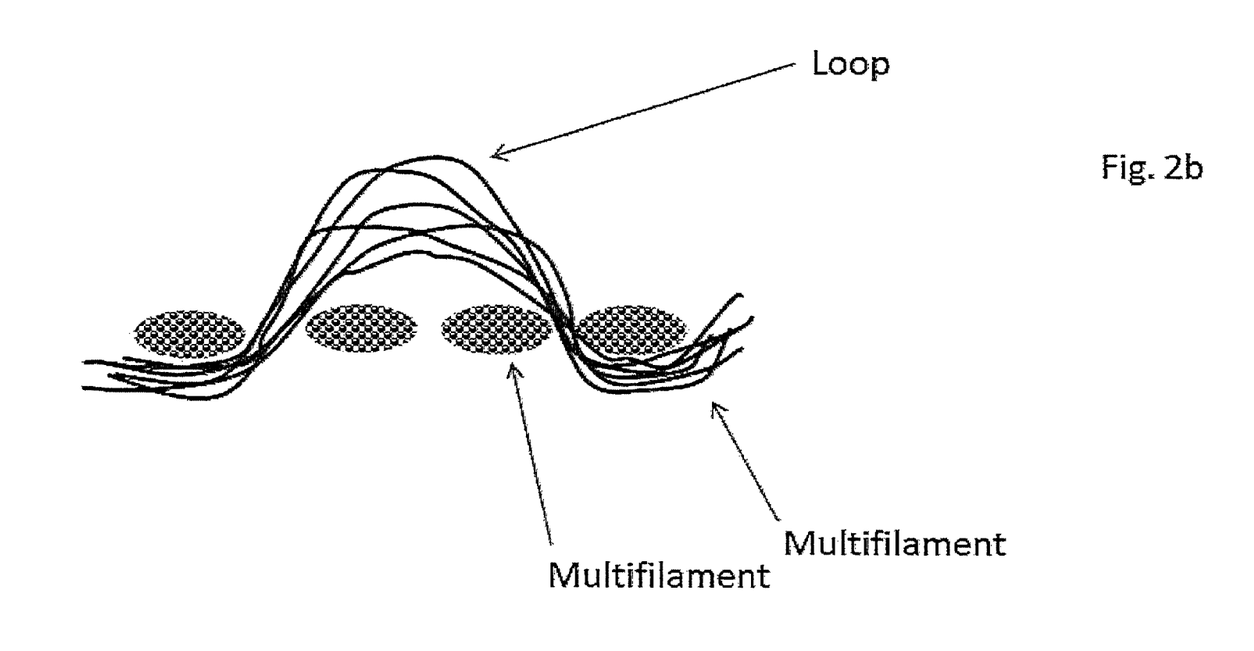
FIG. 2b shows a schematic cross-sectional view of loops formed from a twill of which a warp passes over two wefts.
Figure 2C:
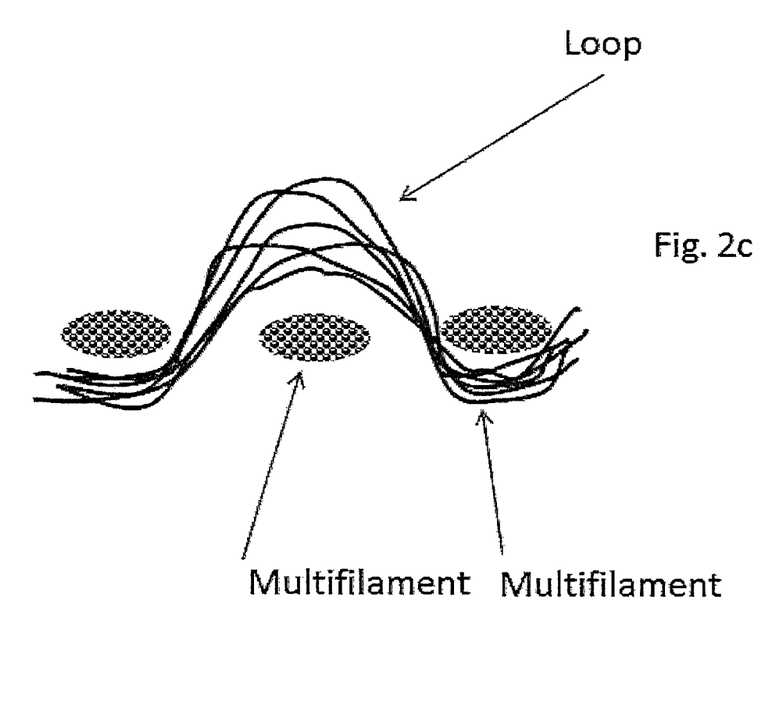
FIG. 2c shows a schematic cross-sectional view of loops formed from a plain weave.

The artificial blood vessel comprises a tubular woven fabric, and the multifilament yarn B forms loops on the inner wall surface of the tubular woven fabric. First, a warp yarn made from the above-mentioned material and having the above-mentioned fineness is warped and set on a weaving machine, and a weft yarn is then prepared in the same manner. As the weaving machine, a water jet loom, an air jet loom, a repier loom, a shuttle loom or the like can be used. Among these, a shuttle loom by which a tubular yarn having a narrow width can be woven satisfactorily can be used preferably. As the tubular woven fabric structure composed of the multifilament yarns A and B, a woven fabric such as a plain-woven fabric, as shown in FIG. 2c, a twill-woven fabric, as shown in FIG. 2b, a satin-woven fabric, as shown in FIG. 2a, a variation of a plain-woven fabric, a twill-woven fabric or a satin-woven fabric, or a multi-layer woven fabric can be used. In a woven structure in which a warp yarn (or a weft yarn) and multiple weft yarns (or warp yarns) do not together form crimps, e.g. a satin-woven structure, i.e., a woven structure in which a warp yarn (or a weft yarn) strides across multiple weft yarns (or warp yarns), the parts (i.e., parts at which the yarn strides across the multiple yarns) get off and are likely to loosen. In this manner, loops are formed. Therefore, it is preferred to weave such that the loops on the inner wall surface of the tubular woven fabric can be formed from the filament B.

A typical means to be employed as a method of forming the loops is, for example, to produce a pile woven fabric. The loops may be ones having satin structures, or ones formed by a bulking treatment, or ones produced due to the difference in yarn length caused by the application of a heat treatment or a chemical solution treatment. The method may be one of forming the loops utilizing a high-pressure stream of a liquid or a gas such as a water jet stream, an air jet stream or the like.

In a method utilizing a raising treatment, for example, using a raising machine, a method using a shearing machine or a method of rubbing with a sand paper, breakage of single fibers or formation of fluffs tends to occur easily.

In the artificial blood vessel, from the viewpoint of the achievement of an excellent anastomosing property, it is preferred that the loops exist in a dispersed state and/or an irregularly interlacing state. The expression, "the loops exist in a dispersed state" refers to a matter that the loops are not concentrated in a specific area but exist in a dispersed manner, and the expression, "the loops exist in an irregularly interlacing state" refers to a matter that a specific pattern of the arrangement of the interlacing parts is not repeated regularly but the interlacing parts exist irregularly in the multifilaments.

Various methods can be employed for the loops to exist in a dispersed state or an irregularly interlacing state. A method utilizing a high-pressure stream of a liquid is effective. Particularly, a method utilizing a water jet stream is preferred, from the viewpoint of uniformity of processing, safety and economic advantages.

The multifilament yarn A and the multifilament B are not limited with respect to the use thereof as either a warp yarn or a weft yarn, and may be used properly. In the artificial blood vessel, from the viewpoint of the colonization of cells and retention of strength, it is preferred that the ratio of the single fibers constituting the multifilament yarn B in the single fibers contained in the tubular woven fabric is 40% or more, more preferably 50% or more. This ratio is preferably 80% or less, more preferably 70% or less, from the viewpoint that sufficient strength and sufficient water permeability required for an artificial blood vessel having a medium or small diameter can be achieved.

The ratio of the number of the single fibers constituting the multifilament A to the number of the single fibers constituting the multifilament B is preferably such a ratio that the number of the single fibers constituting the multifilament B is 0.66 or more, more preferably 1 or more, when it is assumed that the multifilament A is composed of one single filament from the viewpoint of the colonization of cells. The ratio of the number of the multifilament B is preferably 6 or less, more preferably 4 or less, from the viewpoint of retention of strength and water permeability.

Hereinbelow, the means for adjusting the ratio of the number of single fibers constituting the multifilament A to the number of single fibers constituting the multifilament B to a desired value will be described. To adjust the ratio of warp yarns to a desired value, it may be possible to produce warp yarn beams in a double-beam system, respectively, using a multifilament A and a multifilament B (or a fiber that can have the same fiber fineness as that of the multifilament B when processed into ultrafine fibers after weaving) each having a predetermined single fiber fineness and a predetermined total fiber fineness. To adjust the ratio of weft yarns to a desired value, it may be possible to produce the weft yarns respectively using the multifilament A and the multifilament B (or a fiber that can have the same fiber fineness as that of the multifilament B when processed into ultrafine fibers after weaving). As a basic weaving method, any known means can be employed.

In the artificial blood vessel, the thickness of a wall constituting the tubular woven fabric is 50 μm to 250 μm, and preferably 100 to 200 μm from the viewpoint of water permeability and flexibility. When the wall thickness is 50 μm or more, a sufficient water permeability and blood permeability both required for an artificial blood vessel having a medium or small diameter can be achieved. When the wall thickness is 250 μm or less, sufficient flexibility required for an artificial blood vessel having a medium or small diameter can be achieved.

The artificial blood vessel preferably has a water permeability of 500 ml/min·cm$^2$·120 mmHg (16 kPa) or less. This value is preferred, because endothelial cells and capillary vessels can easily penetrate through gaps between fibers in the artificial blood vessel and, therefore, endothelial tissue can be easily formed. The water permeability is more preferably 400 ml/min·cm$^2$·120 mmHg (16 kPa) or less, particularly preferably 300 to 200 ml/min·cm$^2$·120 mmHg (16 kPa). Water permeability is expressed by the amount of water that passes through gaps between fibers in a 1 cm$^2$-wide cloth per minute when a pressure corresponding to 120 mmHg (16 kPa) is applied to the cloth. When water permeability is too high, although endothelial cells and capillary vessels can easily penetrate through gaps between fibers, blood often leaks and bleeding may occur.

To adjust water permeability to a value falling within the above-mentioned range, a method of adjusting the ratios of the number of single fibers in the multifilament yarn A and the multifilament yarn B or a method of adjusting the weave density of the multifilament yarns can be employed. In other words, water permeability of the tubular woven fabric mainly depends on gaps formed between the multifilament yarns and, therefore, the gaps between the multifilament yarns can be controlled and a tubular woven fabric having a desired water permeability can be produced by adjusting the constituent ratios of the multifilament yarn A and the multifilament yarn B or adjusting the weave density of the multifilament yarns.

The artificial blood vessel preferably has the form of a bellows-type structure for the purpose of achieving a satisfactory shape retention property or preventing occurrences of kinking. The bellows-type structure can be formed by attaching the tubular woven fabric to a screw rod having a sufficiently polished surface, winding a given yarn along screw grooves on the screw rod, and then subjecting the resultant product to a heat treatment without any modification, thereby thermally setting the tubular woven fabric. Alternatively, the bellows may be formed by using a highly shrunk yarn as weft yarns and utilizing the action caused by the difference in shrinkage ratio of the yarn.

The artificial blood vessel preferably further comprises an antithrombogenic material. The impartment of antithrombogenicity to the artificial blood vessel may be carried out, for example, by allowing an anticoagulant substance originated from a living organism such as heparin, low-molecular-weight heparin, urokinase and hirudin, to be supported on the multifilament yarns or by allowing a synthetic anticoagulant substance or a synthetic antiplatelet substance such as argatroban, warfarin, acetylsalicylic acid and ticlopidine, to be supported on the multifilament yarns. Alternatively, it may be possible to allow a hydrophilic polymer such as polyethylene glycol, polyvinyl alcohol and polyvinyl pyrrolidone, to be supported on the multifilament yarns. The method to be employed to allow the support is not particularly limited. For example, a method can be mentioned comprising coating the surfaces of the multifilament yarns using a solution containing the above-mentioned substance or polymer. A method may also be mentioned comprising chemically introducing a reactive functional group into the substance or polymer to immobilize the substance or polymer onto the surfaces of the multifilament yarns through a chemical reaction such as a condensation reaction. A method may also be mentioned comprising immobilizing the substance or polymer through a radical reaction using a high-energy ray. A method may also be mentioned comprising impregnating collagen, a gelatin, a hydrogel or the like with the substance or polymer and filling gaps between the multifilament yarns with the impregnation product. As the method of attaching an ionic compound such as heparin, a method can be mentioned comprising forming a salt from the ionic compound and a counter ion and then coating the surfaces of the multifilament yarns with the salt. A method may also be mentioned comprising binding the counter ion to the surfaces of the multifilament yarns in advance and then binding the ionic compound to the counter ion via an ionic bond through an ionic interaction. A method comprising chemically introducing a reactive functional group into the substance or polymer to immobilize the substance or polymer onto the surfaces of the fibers or a method comprising binding the counter ion to the surfaces of the fibers in advance and then binding to the counter ion via an ionic bond can be employed preferably, because the method enables impartment of highly active antithrombogenicity and retention of steady and long-lasting antithrombogenicity. When antithrombogenicity is to be imparted by any one of the above-mentioned methods, it is possible to allow the substance or polymer to be supported on the multifilament yarns in advance. However, from the viewpoint of production cost, it is preferred to produce the tubular woven fabric and then allow the substance or polymer to be supported on the tubular woven fabric.

EXAMPLES

Hereinbelow, our artificial blood vessels will be described in more detail with reference to examples.
Measurement Methods
(1) Fineness
Total fineness: A total fineness was determined in accordance with the method described in JIS L 1013 (1999) 8.3.1 A such that a net fineness was measured under a predetermined load of 0.045 [cN/dtex].
Single fiber fineness: A single fiber fineness was calculated by dividing a total fineness by the number of single fibers.
(2) Woven Fabric Thickness
A woven fabric thickness was measured in accordance with JIS L 1096:2010 8.4 such that an artificial blood vessel was allowed to stand for 10 seconds under a pressure of 23.5 kPa to settle the thickness of a wall layer in the artificial blood vessel, and then the thickness of the wall layer was measured at five different points using a thickness measurement machine, and then an average value of the thicknesses measured at the five points was calculated.
(3) Inner Diameter
The inner diameter of a sample was measured in accordance with the guidance described in ISO7198 such that a circular cone having a taper degree ratio of 1/10 or less was placed vertically, then the sample was allowed to fall over the circular cone gently to cover the circular cone, and the diameter of a portion of the circular cone which was in contact with the lower end of the stopped sample was measured.
(4) Water Permeability
A water permeability was determined in accordance with the guidance described in ISO7198 such that water was dropped on the side wall of an artificial blood vessel to apply a water pressure of 120 mmHg (16 kPa) onto the side wall, and the amount of leaked water, which had passed through the artificial blood vessel and had been released from a fixing jig, per unit surface area and per minute (water permeability) was measured.
(5) Kink Resistance
Kink resistance was determined in accordance with the guidance described in ISO7198 such that an artificial blood vessel was looped and a radius at which the kinking of the artificial blood vessel was apparently observed (the radius was also referred to as a "kink radius", hereinbelow) was measured. In the method of judging the kink resistance, a kink radius of 20 mm or less was determined as "excellent", a kink radius of 21 to 40 mm was determined as "good", a kink radius of 41 to 60 mm was determined as "acceptable", and a kink radius of 61 mm or more was determined as "non-acceptable".
(6) Antithrombogenicity
An abdominal aorta in a rat was exfoliated by about 3 cm, both ends of the abdominal aorta were occluded with clamps to shut off blood flow, then a center part of the aorta was cut, the both cut ends were respectively joined to both ends of an artificial blood vessel, then the clamps were removed to restore the blood flow, the artificial blood vessel was excised after 1 week, and the inner wall surface of the artificial blood vessel was observed. In the judging method, an artificial blood vessel which was patent was determined as "excellent" and an artificial blood vessel which was clogged with thrombi was determined as "non-acceptable".

(7) Cell Adhesiveness

An artificial blood vessel was produced, an arbitrary square portion was cut out from the artificial blood vessel or the artificial blood vessel was cut open, and then the square portion or the cut artificial blood vessel was placed on a cell culture petri dish. Bovine vascular endothelial cells were seeded on the artificial blood vessel at a predetermined density, and were then cultured in an incubator. After 3 days, the cells were observed on a phase-contrast microscope and the ratio of an area onto which the cells were adhered was measured at 1% intervals. In the judging method, an artificial blood vessel in which the number of adhered cells was 90% or more was determined as "excellent", an artificial blood vessel in which the number of adhered cells was 70 to 89% was determined as "good", an artificial blood vessel in which the number of adhered cells was 50 to 69% was determined as "acceptable", and an artificial blood vessel in which the number of adhered cells was 49% or less 90% was determined as "non-acceptable", wherein the percentage values were determined relative to the number of cells which were cultured in the petri dish without the artificial blood vessel.

The properties and performances of the artificial blood vessels produced in the examples described below are shown in Tables 1 and 2.

Example 1

As warp yarns and weft yarns (back side yarns) were used a multifilament yarn A which was made from polyester fibers and had a single fiber fineness of 1.38 dtex and a total fineness of 33 dtex and an untwisted multifilament yarn B' which was made from sea-island composite fibers in which a sea component polymer was polyethylene terephthalate copolymerized with sodium 5-sulfoisophthalate and an island component polymer was polyethylene terephthalate (sea/island (by mass)=20/80, wherein the number of the island components was 70) and had a single fiber fineness of 7.3 dtex and a total fineness of 66 dtex. The multifilament B' is one which can be formed into a multifilament B by a treatment for processing into an ultrafine fiber. Using the warp yarns, a warp yarn beam A and a warp yarn beam B' were produced from the multifilament yarn A and the multifilament B', respectively, using a beamer. Using the weft yarns, a weft yarn shuttle A and a weft yarn shuttle B' were produced from the multifilament yarn A and the multifilament B', respectively, using a pirn winder. A tubular woven fabric having a four-shaft satin weave/plain weave type of warp and weft double-layer weave structure was woven such that the ratio of the number of single fibers constituting the multifilament yarn B in the tubular woven fabric became 60%, using a shuttle loom in which the warp yarn beam A and the warp yarn beam B' were set in a double warp yarn beam system and the weft yarn shuttle A and the multifilament B' were set in a double shuttle system. The tubular woven fabric was then further refined at 98° C. The resultant woven fabric was treated in a 4-mass % aqueous sodium hydroxide solution at 98° C. for 20 minutes to completely dissolve and remove the sea component from the above-mentioned sea-island composite fibers, thereby producing an ultrafine multifilament B having a single fiber fineness of 0.08 dtex and a total fineness of 53 dtex. Subsequently, the woven fabric was dried with dry heat at 120° C. and then sterilized. In this manner, an artificial blood vessel was produced comprising a tubular woven fabric, wherein the tubular woven fabric contained single fibers constituting the multifilament yarn B at a ratio of 60% and had an inner diameter of 3 mmφ and a wall thickness of 180 μm.

When the inner wall surface of the artificial blood vessel thus produced was observed on a microscope at a magnification of ×100, we confirmed that the multifilament yarn B formed loops and the loops existed in a dispersed state. The artificial blood vessel had a water permeability of 250 ml/cm²/min, and also had good kink resistance and excellent antithrombogenicity and cell adhesiveness.

Example 2

An artificial blood vessel comprising a tubular woven fabric was produced in the same manner as in Example 1, except that the ratio of the number of single fibers constituting the multifilament yarn B was adjusted to 75%. When the inner wall surface of the resultant artificial blood vessel was observed on a microscope at a magnification of ×100, we confirmed that the multifilament yarn B formed loops and the loops existed in a dispersed state. The artificial blood vessel had a water permeability of 310 ml/cm²/min, and also had excellent kink resistance, antithrombogenicity and cell adhesiveness.

Example 3

An artificial blood vessel comprising a tubular woven fabric was produced in the same manner as in Example 1, except that the ratio of the number of single fibers constituting the multifilament yarn B was adjusted to 30% and the wall thickness was adjusted to 100 μm. When the inner wall surface of the resultant artificial blood vessel was observed on a microscope at a magnification of ×100, we confirmed that the multifilament yarn B formed loops and the loops existed in a dispersed state. The artificial blood vessel had a water permeability of 190 ml/cm²/min, and also had good kink resistance, excellent antithrombogenicity and a practical level of cell adhesiveness.

Example 4

An artificial blood vessel comprising a tubular woven fabric was produced in the same manner as in Example 1, except that the ratio of the number of single fibers constituting the multifilament yarn B was adjusted to 90% and the wall thickness was adjusted to 240 μm. When the inner wall surface of the resultant artificial blood vessel was observed on a microscope at a magnification of ×100, we confirmed that the multifilament yarn B formed loops and the loops existed in a dispersed state. The artificial blood vessel had a water permeability of 470 ml/cm²/min, and also had good kink resistance and excellent antithrombogenicity and cell adhesiveness.

Example 5

An artificial blood vessel comprising a tubular woven fabric was produced in the same manner as in Example 1, except that a multifilament yarn A having a single fiber fineness of 2.13 dtex and a total fineness of 17 dtex was used as warp yarns and weft yarns and the wall thickness was adjusted to 50 μm.

When the inner wall surface of the resultant artificial blood vessel was observed on a microscope at a magnification of Δ100, we confirmed that the multifilament yarn B formed loops and the loops existed in a dispersed state. The artificial blood vessel had a water permeability of 460 ml/cm²/min, and also had excellent kink resistance, antithrombogenicity and cell adhesiveness.

Example 6

An artificial blood vessel comprising a tubular woven fabric was produced in the same manner as in Example 1, except that a multifilament yarn B having a single fiber fineness of 0.05 dtex and a total fineness of 31 dtex was used as warp yarns and weft yarns and the wall thickness was adjusted to 150 µm.

When the inner wall surface of the resultant artificial blood vessel was observed on a microscope at a magnification of ×100, we confirmed that the multifilament yarn B formed loops and the loops existed in a dispersed state. The artificial blood vessel had a water permeability of 300 ml/cm²/min, and also had excellent kink resistance, antithrombogenicity and cell adhesiveness.

Example 7

A tubular woven fabric was produced in the same manner as in Example 1, except that a plain weave/plain weave-type warp and weft double-layer weave structure was employed as the weave structure and that a polyethylene film having a width of 4 mm and a thickness of 0.12 mm was inserted as a material spacer into the resultant tubular woven fabric and then the tubular woven fabric was subjected to a water jet punching treatment under such conditions that the discharge hole diameter was 0.25 mmφ, the discharge hole spacing was 2.5 mm and the pressure was 70 kg/cm² to thereby form loops.

When the inner wall surface of the resultant artificial blood vessel was observed on a microscope at a magnification of ×100, we confirmed that the multifilament yarn B formed loops and the loops existed in a dispersed and irregularly interlacing state. The artificial blood vessel had a water permeability of 140 ml/cm²/min, and also had good kink resistance and excellent antithrombogenicity and cell adhesiveness.

Example 8

An artificial blood vessel comprising a tubular woven fabric was produced in the same manner as in Example 1, except that the inner diameter of the artificial blood vessel was adjusted to 7.5 mmφ. When the inner wall surface of the resultant artificial blood vessel was observed on a microscope at a magnification of ×100, we confirmed that the multifilament yarn B formed loops and the loops existed in a dispersed state. The artificial blood vessel had a water permeability of 200 ml/cm²/min, and also had good kink resistance and excellent antithrombogenicity and cell adhesiveness.

Example 9

The tubular woven fabric produced in Example 1 was subjected to a bellows processing. In the bellows processing, a stainless bar having a screw formed thereon was allowed to pass through the tubular woven fabric and then a stainless wire was wound around the outside of the tubular woven fabric along the depressed part of the screw. While keeping this state, the sample was allowed to stand for 30 minutes in an oven at 180° C. The sample was gradually cooled and then the stainless wire and the stainless bar were removed. In this manner, the tubular woven fabric was formed into a tubular bellows-type structure.

An artificial blood vessel comprising the tubular woven fabric had a water permeability of 250 ml/cm²/min and also had excellent kink resistance, antithrombogenicity and cell adhesiveness.

Example 10

The tubular woven fabric produced in Example 1 was subjected to an antithrombogenic processing. In the antithrombogenic processing, the tubular woven fabric was treated with a 0.5% aqueous sodium hydroxide solution, and was then oxidized with 5% potassium permanganate. Subsequently, polyethyleneimine (molecular weight: 600, Wako Pure Chemical Industries, Ltd.) was added to the treated tubular woven fabric in the presence of 0.1% 1-(3-dimethylaminopropyl)-3-ethylcarbodiimide to react the fibers in the tubular material with polyethyleneimine. Furthermore, the tubular woven fabric was subjected to a reaction to convert polyethyleneimine immobilized on the surfaces of the fibers into a quaternary ammonium salt at 50° C. in a 1% ethyl bromide solution in methanol. Finally, the tubular woven fabric was immersed in a 0.8% aqueous heparin sodium (Wako Pure Chemical Industries, Ltd.) solution at 70° C. to bind heparin onto the tubular woven fabric via an ionic bond. The resultant product was an antithrombogenic tubular object that was able to be used as an artificial blood vessel. The artificial blood vessel thus produced had better antithrombogenicity compared with the artificial blood vessel produced in Example 1, also had a water permeability of 240 ml/cm²/min and kink resistance, and also had excellent cell adhesiveness.

Comparative Example 1

An artificial blood vessel comprising a tubular woven fabric was produced in the same manner as in Example 1, except that a multifilament yarn A having a single fiber fineness of 1.50 dtex and a total fineness of 84 dtex was used as warp yarns and weft yarns and the wall thickness was adjusted to 250 µm.

When the inner wall surface of the resultant artificial blood vessel was observed on a microscope at a magnification of ×100, we confirmed that the multifilament yarn B formed loops. However, the water permeability of the artificial blood vessel was 660 ml/cm²/min, which was non-acceptable for use as an artificial blood vessel having a medium or small diameter.

Comparative Example 2

An artificial blood vessel comprising a tubular woven fabric was produced in the same manner as in Example 1, except that the wall thickness was adjusted to 310 µm. When the inner wall surface of the resultant artificial blood vessel was observed on a microscope at a magnification of ×100, we confirmed that the multifilament yarn B formed loops. However, the water permeability of the artificial blood vessel was 600 ml/cm²/min, which was non-acceptable for use as an artificial blood vessel having a medium or small diameter.

Comparative Example 3

An artificial blood vessel comprising a tubular woven fabric was produced in the same manner as in Example 1, except that the wall thickness was adjusted to 310 µm. When the inner wall surface of the resultant artificial blood vessel was observed on a microscope at a magnification of ×100, we confirmed that the multifilament yarn B formed loops. However, the kink resistance of the artificial blood vessel was non-acceptable for use as an artificial blood vessel having a medium or small diameter.

Comparative Example 4

An artificial blood vessel comprising a tubular woven fabric was produced in the same manner as in Example 1, except that a multifilament yarn B having a single fiber fineness of 0.23 dtex and a total fineness of 33 dtex was used as warp yarns and weft yarns.

When the inner wall surface of the resultant artificial blood vessel was observed on a microscope at a magnification of ×100, we confirmed that the multifilament yarn B formed loops. However, the cell adhesiveness of the artificial blood vessel was non-acceptable for use as an artificial blood vessel having a medium or small diameter.

Comparative Example 5

An artificial blood vessel comprising a tubular woven fabric was produced in the same manner as in Example 1, except that the wall thickness was adjusted to 30 µm. When the inner wall surface of the resultant artificial blood vessel was observed on a microscope at a magnification of ×100, we confirmed that the multifilament yarn B formed loops. However, the water permeability of the artificial blood vessel was 900 ml/cm$^2$/min, which was non-acceptable for use as an artificial blood vessel having a medium or small diameter.

Comparative Example 6

An artificial blood vessel comprising a tubular woven fabric was produced in the same manner as in Example 1, except that a multifilament yarn B having a single fiber fineness of 0.08 dtex and a total fineness of 84 dtex was used as warp yarns and weft yarns and the wall thickness was adjusted to 180 µm.

When the inner wall surface of the resultant artificial blood vessel was observed on a microscope at a magnification of ×100, we confirmed that the multifilament yarn B formed loops. However, the loops were protruded excessively from the inner wall surface and, with respect to antithrombogenicity, thrombi were formed on the inner wall surface. Therefore, the artificial blood vessel was non-acceptable for use as an artificial blood vessel having a medium or small diameter.

Comparative Example 7

The tubular woven fabric produced in Example 1 was subjected to a raising processing using a raising machine, thereby producing an artificial blood vessel comprising a tubular woven fabric.

When the inner wall surface of the resultant artificial blood vessel was observed on a microscope, the loops of the multifilament yarn B were collapsed through the raising processing, and fluffs were formed on the inner wall surface. When the artificial blood vessel was evaluated, thrombi were formed on the inner wall surface in the antithrombogenicity test. Therefore, the artificial blood vessel was non-acceptable for use as an artificial blood vessel having a medium or small diameter.

TABLE 1

| | | Multifilament A | | Multifilament B | |
| --- | --- | --- | --- | --- | --- |
| | Weaving structure | Single fiber fineness | Total fineness (dtex) | Single fiber fineness | Total finesss (dtex) |
| Example 1 | Four-shaft satin weave/Plain weave | 1.38 | 33 | 0.08 | 53 |
| Example 2 | Four-shaft satin weave/Plain weave | 1.38 | 33 | 0.08 | 53 |
| Example 3 | Four-shaft satin weave/Plain weave | 1.38 | 33 | 0.08 | 53 |
| Example 4 | Four-shaft satin weave/Plain weave | 1.38 | 33 | 0.08 | 53 |
| Example 5 | Four-shaft satin weave/Plain weave | 2.13 | 17 | 0.08 | 53 |
| Example 6 | Four-shaft satin weave/Plain weave | 1.38 | 33 | 0.05 | 31 |
| Example 7 | Plain weave/Plain weave | 1.38 | 33 | 0.08 | 53 |
| Example 8 | Four-shaft satin weave/Plain weave | 1.38 | 33 | 0.08 | 53 |
| Example 9 | Four-shaft satin weave/Plain weave | 1.38 | 33 | 0.08 | 53 |
| Example 10 | Four-shaft satin weave/Plain weave | 1.38 | 33 | 0.08 | 53 |
| Comparative Example 1 | Four-shaft satin weave/Plain weave | 1.5 | 84 | 0.08 | 53 |
| Comparative Example 2 | Four-shaft satin weave/Plain weave | 2.33 | 56 | 0.08 | 53 |
| Comparative Example 3 | Four-shaft satin weave/Plain weave | 1.38 | 33 | 0.08 | 53 |
| Comparative Example 4 | Four-shaft satin weave/Plain weave | 1.38 | 33 | 0.23 | 33 |
| Comparative Example 5 | Four-shaft satin weave/Plain weave | 1.38 | 33 | 0.08 | 53 |

TABLE 1-continued

| | | Thickness of wall (μm) | Inner diameter (mmφ) | Surface processing | Bellows processing | Antithrombogenic processing |
|---|---|---|---|---|---|---|
| Comparative Example 6 | Four-shaft satin weave/Plain weave 1.38 33 0.08 84 | | | | | |
| Comparative Example 7 | Four-shaft satin weave/Plain weave 1.38 33 0.08 53 | | | | | |

| | Ratio of Multi-filament B (%) | Thickness of wall (μm) | Inner diameter (mmφ) | Surface processing | Bellows processing | Antithrombogenic processing |
|---|---|---|---|---|---|---|
| Example 1 | 60 | 180 | 3 | No | No | No |
| Example 2 | 75 | 180 | 3 | No | No | No |
| Example 3 | 30 | 100 | 3 | No | No | No |
| Example 4 | 90 | 240 | 3 | No | No | No |
| Example 5 | 60 | 50 | 3 | No | No | No |
| Example 6 | 60 | 150 | 3 | No | No | No |
| Example 7 | 60 | 180 | 3 | Interlacing | No | No |
| Example 8 | 60 | 220 | 7.5 | No | No | No |
| Example 9 | 90 | 240 | 3 | No | Yes | No |
| Example 10 | 60 | 220 | 3 | No | No | Yes |
| Comparative Example 1 | 60 | 230 | 3 | No | No | No |
| Comparative Example 2 | 60 | 240 | 3 | No | No | No |
| Comparative Example 3 | 60 | 310 | 3 | No | No | No |
| Comparative Example 4 | 60 | 180 | 3 | No | No | No |
| Comparative Example 5 | 45 | 30 | 3 | No | No | No |
| Comparative Example 6 | 60 | 180 | 3 | No | No | No |
| Comparative Example 7 | 60 | 180 | 3 | Raising (Loop cut) | No | No |

TABLE 2

| | Water permeability (ml/cm²/min) | Kink resistance | Antithrombogenicity | Cell adhesiveness |
|---|---|---|---|---|
| Example 1 | 250 | Good | Excellent | Excellent |
| Example 2 | 310 | Good | Excellent | Excellent |
| Example 3 | 190 | Good | Excellent | Acceptable |
| Example 4 | 470 | Good | Excellent | Excellent |
| Example 5 | 460 | Good | Excellent | Excellent |
| Example 6 | 300 | Good | Excellent | Excellent |
| Example 7 | 190 | Good | Excellent | Excellent |
| Example 8 | 360 | Good | Excellent | Excellent |
| Example 9 | 180 | Excellent | Excellent | Excellent |
| Example 10 | 240 | Good | Excellent | Excellent |
| Comparative Example 1 | 660 | Good | Excellent | Excellent |
| Comparative Example 2 | 600 | Good | Excellent | Excellent |
| Comparative Example 3 | 180 | Non-acceptable | Excellent | Excellent |
| Comparative Example 4 | 420 | Good | Excellent | Non-acceptable |
| Comparative Example 5 | 900 | Good | Excellent | Excellent |
| Comparative Example 6 | 300 | Good | Non-acceptable | Excellent |
| Comparative Example 7 | 250 | Good | Non-acceptable | Excellent |

The invention claimed is:

1. An artificial blood vessel comprising a tubular woven fabric composed of a multifilament yarn A comprising a first polyester and a multifilament yarn B comprising a second polyester, has an inner diameter of 8 mm or less and a layer thickness of 50 μm or more and 250 μm or less, and has a water permeability of 400 ml/min·cm²·120 mmHg (16 kPa) or less, wherein the multifilament yarn A has a single fiber fineness of 1.0 dtex or more and a total fineness of 33 dtex or less, the multifilament yarn B has a single fiber fineness of 0.08 dtex or less and a total fineness of 66 dtex or less, the multifilament yarn B forms loops on an inner wall surface of the tubular woven fabric, and a number of single fibers in the multifilament yarn B is 40% to 80% of a number of single fibers that constitute the tubular woven fabric.

2. The artificial blood vessel according to claim 1, comprising a bellows-type structure.

3. The artificial blood vessel according to claim 2, further comprising an antithrombogenic material.

4. The artificial blood vessel according to claim 1, further comprising an antithrombogenic material.

* * * * *